United States Patent
Naka et al.

(10) Patent No.: US 7,435,981 B2
(45) Date of Patent: Oct. 14, 2008

(54) ELECTRON BEAM STERILIZER

(75) Inventors: Toshiaki Naka, Kanazawa (JP);
Yukinobu Nishino, Kanazawa (JP)

(73) Assignee: Shibuya Kogyo Co., Ltd.,
Kanazawa-shi, Ishikawa-ken (JP)

( * ) Notice: Subject to any disclaimer, the term of this patent is extended or adjusted under 35 U.S.C. 154(b) by 319 days.

(21) Appl. No.: 11/450,487

(22) Filed: Jun. 9, 2006

(65) Prior Publication Data
US 2007/0018115 A1    Jan. 25, 2007

(30) Foreign Application Priority Data
Jun. 21, 2005    (JP) .............................. 2005-181087

(51) Int. Cl.
*A61N 5/00*    (2006.01)
*G21G 5/00*    (2006.01)
(52) U.S. Cl. .............................. 250/492.3; 250/454.11;
250/492.1; 250/493.1; 250/208.1; 250/505.1;
422/22; 422/24; 422/119; 422/56; 422/61;
426/392; 426/398; 426/35; 426/186.04; 204/157.15;
436/1; 436/166
(58) Field of Classification Search ............... 250/492.3,
250/454.11, 492.1, 493.1, 208.1, 505.1; 422/22,
422/24, 119, 56, 61; 426/392, 398, 35, 186.04;
204/157.15; 436/1, 166
See application file for complete search history.

(56) References Cited

U.S. PATENT DOCUMENTS 4,652,763 A * 3/1987 Nablo ...................... 250/492.3

FOREIGN PATENT DOCUMENTS

| JP | 11-001212 | 1/1999 |
| JP | 11-137645 | 5/1999 |
| JP | 11137645 A * | 5/1999 |
| JP | 2003-192095 | 7/2003 |
| JP | 2003192095 A * | 7/2003 |
| WO | WO 01/23007 A1 | 4/2001 |

\* cited by examiner

*Primary Examiner*—Jack I. Berman
*Assistant Examiner*—Meenakshi S Sahu
(74) *Attorney, Agent, or Firm*—Flynn, Thiel, Boutell & Tanis, P.C.

(57) ABSTRACT

A plurality of vessel holder means 14 are mounted around a revolving body 12 at an equal circumferential spacing. Each vessel holder means 14 includes two holders 26, 26 for carrying two vessels 4, 4 in vertical alignment. A path along which the revolving body 12 revolves contains an inversion interval C-D and an upright transfer interval D-B and A-C. Inversion means 16 which inverts the vessel holder means 14 about a tangential axis O1 is located within the inversion interval C-D while an electron beam irradiator 24 is located within the upright transfer interval A-C. Vessels which are fed at a vessel feed position A and carried by the holders 26 are subject to the irradiation of the electron beam at an electron beam irradiation position E, then inverted, and when it reaches the electron beam irradiation position E again, the opposite surface is subject to the irradiation of the electron beam. Vessels 4 are inverted again and then discharged at a vessel discharge position B. Using a single electron beam irradiator 24, the entire surface of the vessel 4 being conveyed can be sterilized by irradiation of the electron beam.

6 Claims, 7 Drawing Sheets

ELECTRON BEAM STERILIZER

BACKGROUND OF THE INVENTION AND RELATED ART STATEMENT

The present invention relates to an electron beam sterilizer which sterilizes vessels being conveyed by irradiation with an electron beam.

An electron beam sterilizer which sterilizes vessels being conveyed by irradiation with an electron beam is known in the art (see Japanese Laid-Open Patent Application No. 11-137645 or No. 11-1212, for example). "Electron beam sterilizer for empty plastic vessels" according to the invention disclosed in the first cited Application comprises a feeder mechanism which feeds empty plastic vessels, a turning mechanism, an electron beam irradiation mechanism, and a discharge mechanism which discharges empty plastic vessels subjected to the electron beam irradiation.

The purpose of the turning mechanism is to secure empty plastic vessels fed from the feeder mechanism by applying a vacuum suction thereto and to cause a turning motion and a revolving motion about individual axes of the empty plastic vessels while they are secured, and the turning mechanism comprises a plurality of turntables on which the empty plastic vessels are secured and a turntable drive. The electron beam irradiation mechanism sterilizes the empty plastic vessels by irradiating them with the electron beam from the inner periphery of and in synchronism with the turning mechanism. In the arrangement of the cited invention, the electron beam irradiation mechanism includes electron beam irradiators which are equal in number to the number of turntables disposed on the turning orbit of the turning mechanism.

"Sterilizer for vessels utilizing electron beam" disclosed in the second sited Application comprises an electron beam generator disposed in a vertical position within a sterilization processing chamber, and vessel conveying means extending from the inlet to the outlet of the sterilization processing chamber. There is disposed revolution imparting means which causes a vessel to revolve at a location in front of the electron beam generator.

According to the sterilizer shown in the second citation, vessels proceed through the sterilization processing chamber on vessel conveying means (air conveyor), and are subject to a revolution as they reach the revolution imparting means. Vessels which are conveyed while revolving pass an irradiation window of the electron beam generator while revolving about their axes. Vessels which are successively conveyed in this manner are sterilized by irradiation with the electron beam as they pass in front of the irradiation window while being imparted with a revolution by the revolution imparting means, and are subsequently discharged out of the sterilization processing chamber.

In the arrangement of the invention disclosed in the first cited Application, there is a need for the provision of as many electron beam irradiators as the number of the turntables on which the vessels are secured, leading to a problem that the arrangement is expensive and bulky as a whole. By contrast, in the arrangement of the invention disclosed in the second cited Application, the electron beam irradiator is provided at a single location, but the revolution is imparted to the vessels for irradiating the electron beam around the full periphery of the vessels. The arrangement that the vessels are caused to revolve in the course of the air conveyance leads to a problem that a high speed operation is inhibited.

OBJECT AND SUMMARY OF THE INVENTION

Accordingly, it is an object of the present invention to provide an electron beam sterilizer which enables a sterilization around the full periphery of vessels with a single electron beam irradiator to simplify the arrangement and to achieve a cost reduction while allowing a high speed operation to be achieved.

Above object is accomplished by providing an electron beam sterilizer which sterilizes vessels being conveyed by irradiation with an electron beam and which comprise vessel holder means including a pair of holders which carry two vessels in vertical alignment, transfer means on which a plurality of vessel holder means are mounted at an equal interval and are cyclically transferred, inversion means for inverting the vessel holder means by rotating it about an axis parallel to a direction in which the transfer means advances, and an electron beam irradiator capable of irradiating the electron beam across the upper and the lower end of the two vessels which are carried in vertical alignment by the vessel holder means, the arrangement being such that a transfer path of the transfer means extends from a vessel feed position to a vessel discharge position and includes an inversion interval where the inversion means inverts the vessel holder means and an upright transfer interval where the vessels in vertical alignment are transferred in an upright position, the electron beam irradiator having an electron beam irradiation position which is chosen within the upright transfer interval, the vessels which are fed through the vessel feed position being discharged at the vessel discharge position after passing through the electron beam irradiation position and the inversion interval twice.

DETAILED DESCRIPTION OF PREFERRED EMBODIMENTS

Figure 1:
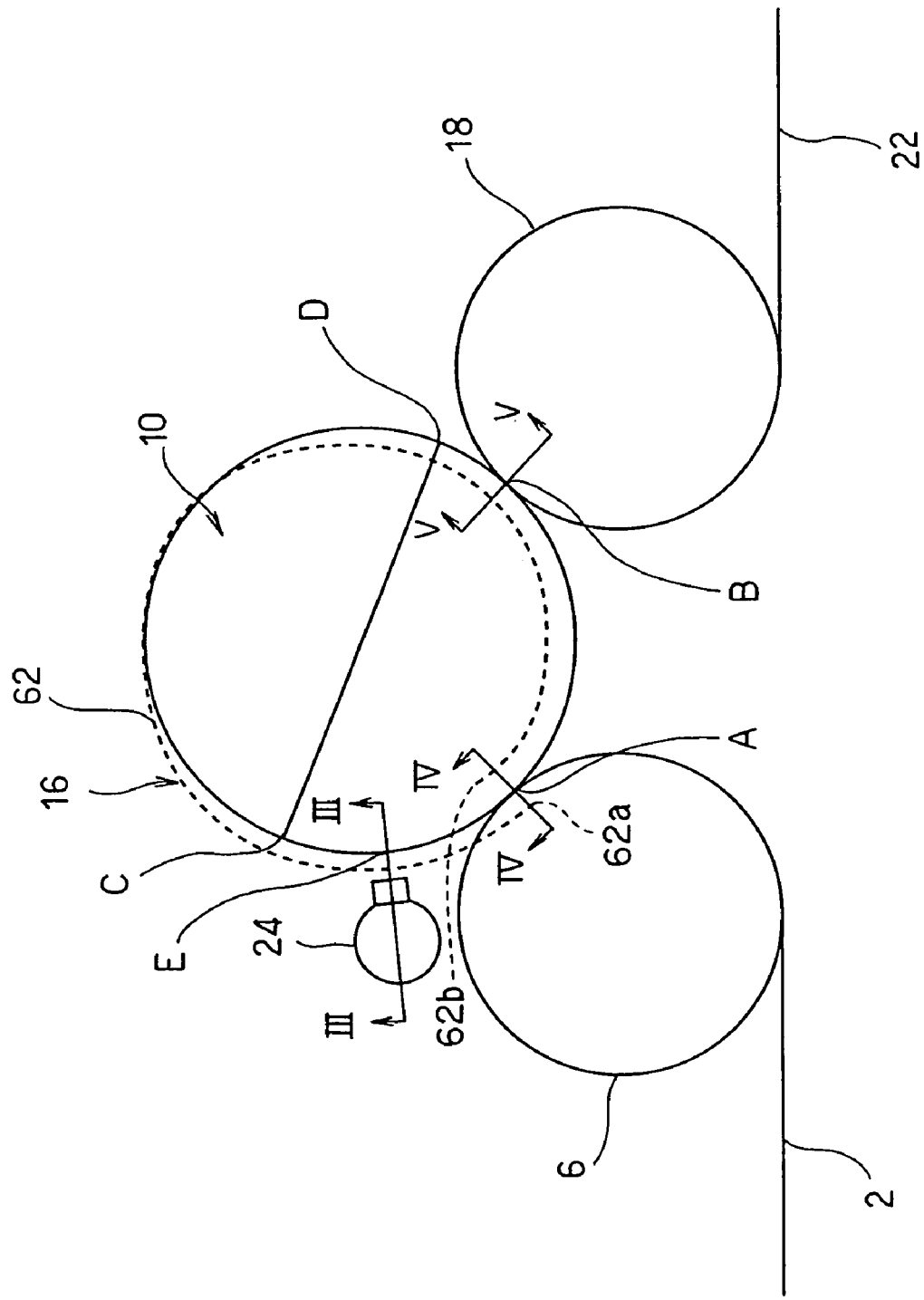
FIG. 1 is a plan view showing the layout of an electron beam sterilizer according to one embodiment of the present invention.

Several embodiments of the present invention shown in the drawings will now be described. Vessels 4 such as PET bottles (see FIGS. 2-5 which will be described later) which are conveyed by an air conveyor 2, representing vessel feed means, are carried by grippers 8 (see FIG. 4) of a feed gripper wheel 6 and are rotatively conveyed to be fed to an electron beam sterilizer 10 (a feed position where vessels 4 are fed from the feed gripper wheel 6 to the electron beam sterilizer 10 is indicated by a character A in FIG. 1).

The electron beam sterilizer 10 comprises a plurality of vessel holder means 14 which are mounted around the outer periphery of a revolving body (transfer means) 12 at an equal circumferential spacing, and vessels 4 which are fed from the feed gripper wheel 6 are carried by the vessel holder means 14. As the revolving body 12 rotates, the vessel holder means 14 are rotatively transferred, thus rotatively conveying the vessels 4 which are carried thereby. Inversion means 16 which inverts the vessel holder means 14 which carries the vessels 4 is provided on a path of conveyance of the vessels 4, and accordingly, a vessel 4 which is fed in an erect position (where a mouth 4a of the vessel 4 is directed upward) can be inverted by the inversion means 16 to its inverted position. Subsequently, after the vessel 4 is rotatively conveyed in its inverted position, it is inverted again into the erect position by the inversion means 16, and then delivered to a gripper 20 of a discharge gripper wheel 18 (see FIG. 5) to be discharged and fed to a succeeding downstream step by an air conveyor 22. In this embodiment, a vessel 4 is handed from the gripper 8 of the feed gripper wheel 6 to the vessel holder means 14 of the electron beam sterilizer 10 at a vessel feed position (indicated by position A in FIG. 1), inverted twice during substantially two revolutions of the revolving body 12, and handed to the gripper 20 of the discharge gripper wheel 18 at a vessel discharge position (indicated by position B in FIG. 1) to be discharged by the air conveyor 22.

Figure 3:
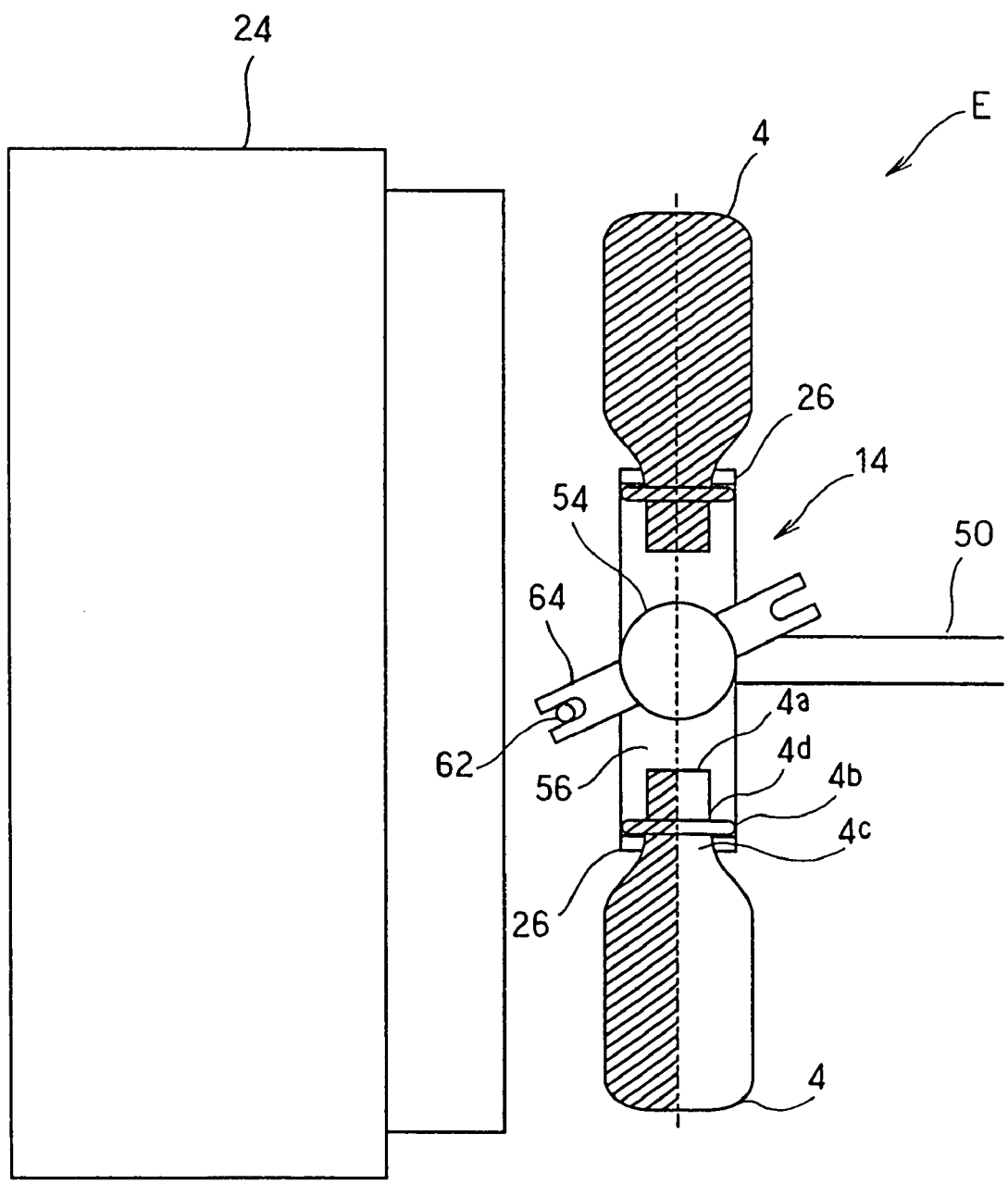
FIG. 3 is a cross section taken along the line III-III shown in FIG. 1.

The electron beam sterilizer 10 comprises an irradiation unit 24 which is disposed toward the outer periphery of the sterilizer at a location which is slightly downstream of the vessel feed position A as viewed in the direction in which the vessel 4 is conveyed (see FIGS. 1 and 3). As will be described later, the vessel holder means 14 includes a pair of upper and lower vessel holders 26, 26, and the irradiation unit 24 has a sufficient length which permits the pair of upper and lower vessels 4 which are carried in upright position by the pair of vessel holders 26 to be simultaneously irradiated by the electron beam.

Figure 2:
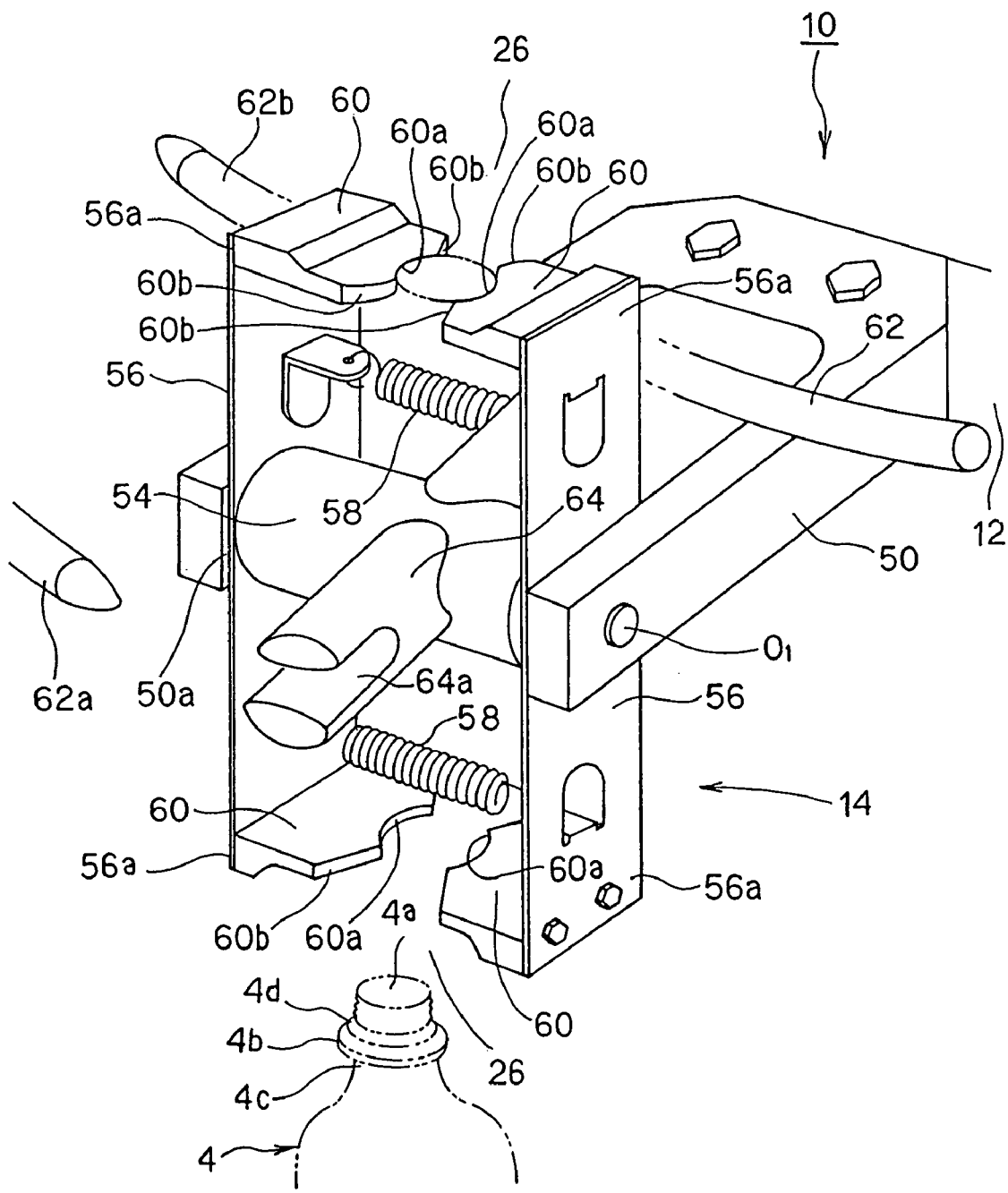
FIG. 2 is a perspective view of vessel holder means contained in the electron beam sterilizer.

The arrangement of the electron beam sterilizer 10 will now be described in detail with reference to FIGS. 1 to 5. A plurality of vessel holder means 14 are disposed around the outer periphery of the revolving body 12 (not entirely shown) at an equal circumferential spacing. As shown in FIG. 2, channel-shaped mounting members 50 are mounted around the outer periphery of the revolving body 12 at an equal circumferential spacing and horizontally secured with an opening 50a of the mounting member directed radially outward of the revolving body 12, and the vessel holder means 14 are mounted on each of the plurality of mounting members 50. Each vessel holder means 14 includes a pair of vessel holders 26, 26. While the vessel holder means 14 used in this embodiment is constructed in the similar manner as the vessel holder means disclosed in Japanese Laid-Open Patent Application No. 2003-192095 filed by the present applicant, it may also be constructed in a different manner.

In the present embodiment, each of the pair of vessel holders 26, 26 are constructed in the identical manner, and accordingly, corresponding parts are designated by like characters. A pair of parallel leaf springs (support plates) 56 which are centrally secured to the opposite ends of a rod 54 are rotatably supported in the opening 50a of the mounting member 50. As mentioned previously, the mounting member 50 is fixedly mounted around the outer periphery of the revolving body 12 so as to be directed in the radial direction, and accordingly, the rod 54 which is supported across the opening 50a is directed in the tangential direction of the revolving body 12. In addition, a pair of springs 58 are connected across the both leaf springs 56 on the opposite sides of the rod 54 to urge the ends 56a of the both leaf springs 56 toward each other normally. In addition, a pair of holding plates 60 which oppose each other are mounted on the respective ends 56a (upper and lower end as viewed in FIG. 2) of the pair of leaf springs 56, and define the vessel holders 26, 26. The opposing faces of the holding plates 60 are each centrally formed with an arcuate concave surface 60a which abuts against a neck of the vessel 4 (which is a portion 4c disposed below a flange 4b) and are each formed with guide surfaces 60b which extend outwardly to be further spaced from each other at locations which are disposed on the opposite sides of the concave surface 6Oa.

The holding plates 60 on the opposite sides which define the vessel holders 26, 26 are secured to the ends 56a of the pair of leaf springs 56 and are attracted toward each other by the springs 58, whereby the vessel 4 is carried as the portion 4c located below the flange 4b moves between the guide surfaces 60b of the holding plates 60 which are then disposed on the opposite sides to urge the holding plates 60 away from each other to allow the portion 4c to be snapped into the space formed by the arcuate concave surfaces 60a of the holding plates 60, which are then caused to spring back under the resilience of the springs 58. It will be seen that because the guide surfaces 60b are formed on each holding plate 60 on the opposite sides of the arcuate concave surface 60a, an access into the space defined between the opposing arcurate concave surfaces 60a can be achieved through the guide surfaces 60b on either side. The leaf springs 56, the springs 58 and the vessel holders 26, 26 formed by a set of holding plates 60 constitute together the vessel holder means 14. In this embodiment, the vessel holder means 14 is constructed such that the vessel holders 26, 26 are disposed at positions which are symmetrical with respect to the center axis of the central rod 54 or an axis O1 which is disposed tangentially of the revolving body 12 to allow two vessels 4 to be carried in vertical alignment.

Figure 4:
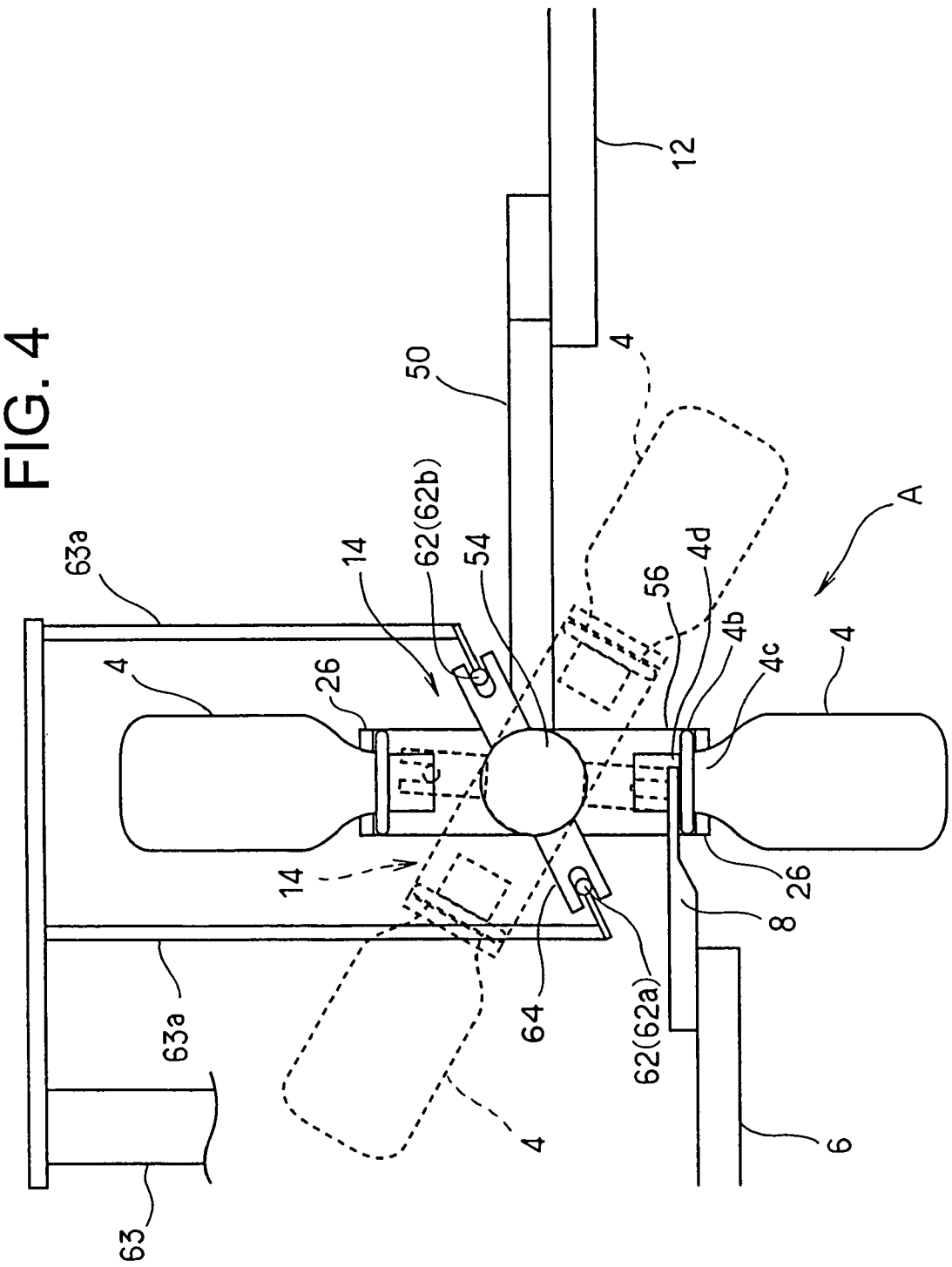
FIG. 4 is a cross section taken along the line IV-IV shown in FIG. 1.
Figure 5:
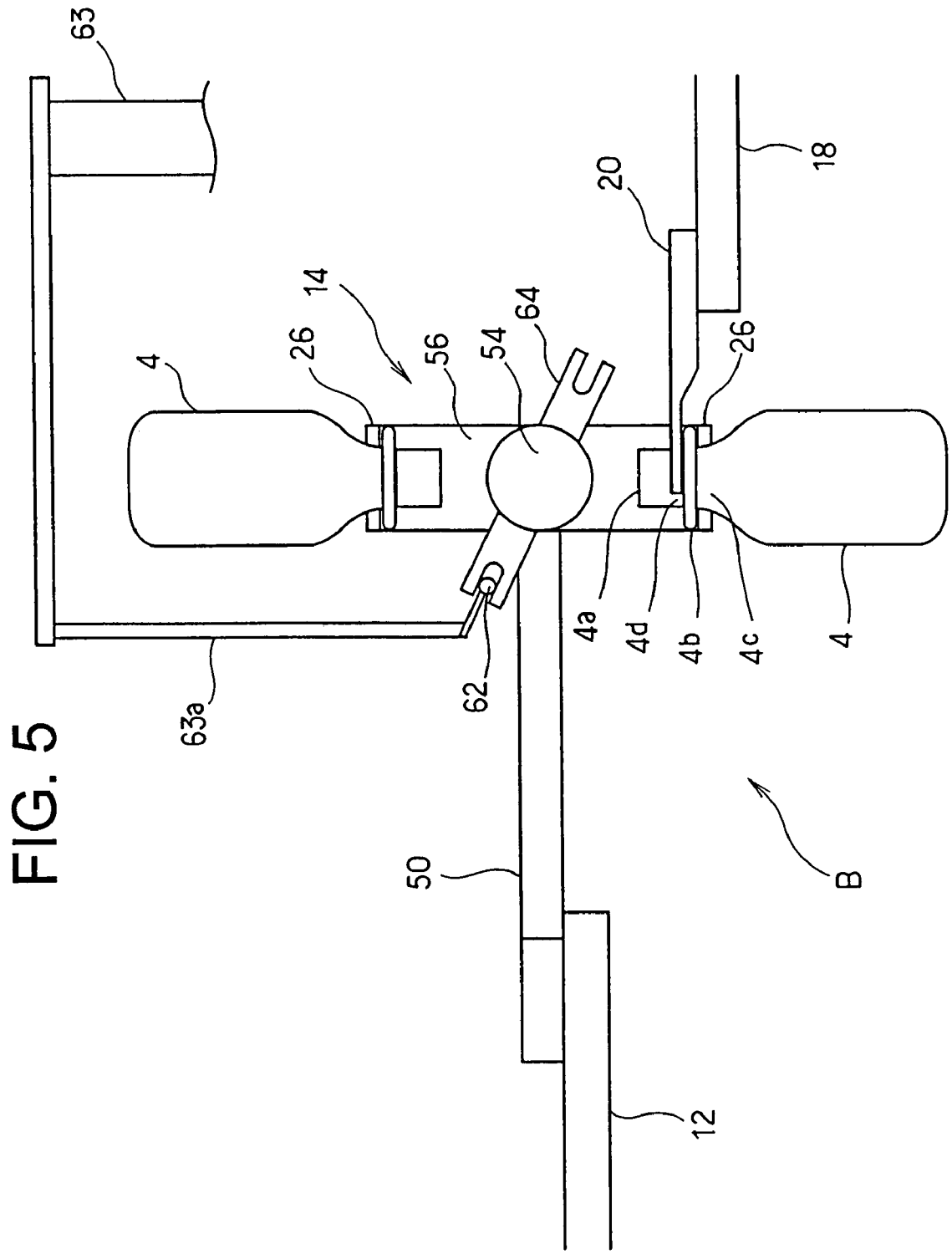
FIG. 5 is a cross section taken along the line V-V shown in FIG. 1.

An engaging member 64 which is formed in its opposite ends with U-shaped recesses 64a adapted to engage a guide rail 62, which will be described later, is secured to the central portion of the rod 54 as viewed in the length direction thereof. As illustrated in FIGS. 2 to 5, the engaging member 64 is mounted as skewed with respect to the leaf springs 56 located on the opposite sides. On the other hand, a guide rail 62 is disposed adjacent to and around the outer periphery of the revolving body 12 for engaging the U-shaped recess 64a in the engaging member 64 to rotate the vessel holder means 14 through about 180° about the axis O1 of the rod 54 so as to interchange upper and lower ones of the pair of vessel holders 26, 26 as the revolving body 12 revolves. The guide rail 62 constitutes the inversion means 16. As illustrated in FIGS. 4 and 5, it is supported by guide rail support means 63a mounted on a stationary stanchion 63 which is disposed externally of the revolving body 12 so as to avoid an interference with the vessels 4 or the vessel holder means 14. The distal end 62a (see FIGS. 1 and 2) of the guide rail 62 which is positioned over the feed gripper wheel 6 (which is located to the left as viewed in FIG. 4) engages the U-shaped recess 64a in the engaging member 64 at the vessel feed position A (see FIGS. 1 and 4) where the vessels 4 are fed from the feed gripper wheel 6 to the electron beam sterilizer 10.

Toward the vessel discharge position B where the vessels 4 are discharged from the electron beam sterilizer 10 to the discharge gripper wheel 18, the guide rail 62 gradually increases its elevation and enters inside the revolving body 12 and then gradually decreases its elevation. In other words, the location of the guide rail 62 is twisted around the position of the rod 54 to rotate through 180°. The vessel holder means 14 and the vessels 4 shown in broken lines in FIG. 4 indicate their conditions in the course of such inversion. As mentioned previously, when the position is changed through 180°, the two vessels 4 assume completely interchanged positions as far as upper and lower vessels are concerned. In the present embodiment, a path section from a position C which is located downstream of the electron beam irradiation position E where the electron beam irradiation means 24 is disposed to a position D which is located one-half perimeter ahead in FIG. 1 represents an inversion interval where the guide rail 62 causes an inversion of the vessel holder means 14 and the two vessels 4 which are carried by the holders 26, 26. Along a path section from the vessel discharge position B to the vessel feed position A, only the upper vessel holder 26 carries the vessel 4. Accordingly, a path section from the position D where the inversion interval ends to the vessel discharge position B and from the vessel feed position A to the position C where the inversion interval begins represents an upright transfer interval where two vessels carried in vertical alignment are transferred while their axes are maintained in the vertical direction. The guide rail 62 and the engaging member 64 of the vessel holder means 14 define the inversion means 16 which causes an inversion of the vessel holder means 14 by rotating it about the tangential axis O1 of the revolving body 12.

The operation of the electron beam sterilizer 10 constructed in the manner mentioned above will now be described. Vessels 4 which are conveyed in suspended form by the vessel feed means (air conveyor) 2 are carried by the gripper 8 of the feed gripper wheel 6 to be rotatively conveyed. In the present embodiment, the gripper 8 of the feed gripper wheel 6 carries a portion 4d of the vessel 4 which is located above the flange 4b formed around the neck of the vessel (see FIG. 4).

As the vessel 4 carried by the gripper 8 of the feed gripper wheel 6 approaches the feed position A to the electron beam sterilizer 10, the portion 4c of the vessel 4 which is disposed below the flange 4b is inserted between the opposing holding plates 60 of one of the pair of upper and lower vessel holders 26, 26 which is then disposed downward (see the lower vessel holder 26 shown in FIG. 4 indicating the vessel feed position A) of the vessel holder means 14 mounted on the channel-shaped mounting members 50 which are secured to the revolving body 12 (transfer means of the electron beam sterilizer 10) at an equal circumferential spacing. It is to be noted that the pair of vessel holders 26, 26 are disposed in vertical alignment as shown in FIG. 4 at the feed position A from the feed gripper wheel 6 to the electron beam sterilizer 10.

Since the both holding plates 60 are secured to the leaf springs 56 and are attracted toward each other by the springs 58, the vessel 4 carried by the gripper 8 of the feed gripper wheel 6 passes between the guide surfaces 60b of the both holding plates 60 by spreading them apart to be fitted between the arcuate concave portions 60a. At the start of the operation of the electron beam sterilizer 10, only the lower holder 26 shown in FIG. 4 carries the vessel 4. On the other hand, the engaging member 64 which is integral with the vessel holder means 14 has its downwardly directed U-shaped recess 64a engaged with the distal end 62a of the guide rail 62. At this point in time, the upwardly directed U-shaped recess 64a is engaged by the distal end 62b of the guide rail 62 (see FIGS. 1 and 4).

As the feed gripper wheel 6 and the revolving body 12 of the electron beam sterilizer 10 both rotate and the gripper 8 and the vessel holder 26 of the vessel holder means 14 move away from each other, the vessel 4 is disengaged from the gripper 8 of the feed gripper wheel 6 and is carried by the vessel holder 26 to be rotatively conveyed as the revolving body 12 of the electron beam sterilizer 10 revolves. It will be noted that a path section short of the inversion start position C which is located downstream of the vessel feed position A to the electron beam sterilizer 10 represents the upright transfer interval, and the electron beam irradiation position E is chosen to be within this interval. The irradiation unit 24 of the electron beam irradiator is disposed so as to correspond to the electron beam irradiation position E and is directed radially inward of the revolving body 12 which forms the electron beam sterilizer 10 (see FIGS. 1 and 3), thus irradiating the electron beam across the upper and the lower end of the passing vessel 4. During this irradiation (the first irradiation with respect to the vessel 4), nearly one-half of the surface of the vessel 4 carried by the lower holder 26 of the vessel holder means 14 which is directed radially outward of the revolving body 12 is sterilized (specifically, hatched portion of the vessel 4 carried by the lower holder 26 as shown in FIG. 3 is sterilized).

As the revolving body 12 continues to rotate, the vessel holder means 14 passes the frontage of the irradiation unit 24, and when it enters the inversion interval C-D, the U-shaped recess 64a in the engaging member 64 moves upward and radially inward in conformity to the configuration of the guide rail 62, whereby the vessel holder means 14 is rotated to interchange the two vessel holders 26, 26 as far as the upper and the lower one are concerned. When the two vessel holders 26, 26 rotate through 180° and are interchanged as far as the upper and the lower holder are concerned, the vessel which is carried by one of the vessel holders located downward as viewed in FIG. 4 is inverted from its lower, erect position to an upper inverted position.

During the time the vessel holder means 14 passes through the inversion interval C-D, the upper and the lower holder 26, 26 rotate through 180° about the rod 54, whereby the vessel which was previously carried by the lower holder 26 to maintain an erect position now assumes a completely inverted position (see the upper vessel 4 shown in FIG. 5). Subsequently, the revolving body 12 of the electron beam sterilizer 10 further rotates to reach the vessel discharge position B. The discharge gripper wheel 18 including a gripper 20 is disposed at the vessel discharge position B, but this gripper 20 is located at an elevation to grip the vessel 4 carried by the lower holder 26, and at the present moment which immediately follows the start of the operation, the lower vessel hold 26 carries no vessel 4, and accordingly, the vessel holder means 14 passes through the discharge position B without any effect.

When the vessel holder means 14 again reaches the vessel feed position A, the gripper 8 of the feed gripper wheel 6 which receives the vessel 4 from the air conveyor 2 to convey it rotatively acts to hand the next vessel 4 to the empty holder 26 of the vessel holder means 14 which now assumes a lower position. At this point, the vessel holder means 14 is in a condition such that the upper and the lower vessel holder 26, 26 each carries the vessel 4. At this time, the two vessels 4 are disposed in vertical alignment with the vessel 4 carried by the lower holder 26 assuming an erect position where the mouth faces upward and the vessel 4 carried by the upper holder 26 assuming an inverted position where the mouth faces downward, as shown in FIG. 4.

The vessel holder means 14 carrying the two vessels 4 in vertical alignment reaches the electron beam irradiation position E where the irradiation unit 24 of the electron beam irradiator is disposed to be subject to the irradiation of the electron beam. The vessel 4 which has been subjected to be irradiation of the electron beam by the irradiation unit 24 during the previous run is now inverted about the rod 54 which is directed in the tangential direction of the revolving body 12 during the inversion interval C-D, and accordingly, the irradiated portion now assumes a position located to the right, as viewed in FIG. 3. Thus, the vessel 4 which passes the electron beam irradiation position E for the second time (or the upper vessel 4 as viewed in FIG. 3) is oriented such that the portion which has not been subject to the irradiation of the electron beam during the previous run (or the portion disposed to the left as viewed in FIG. 3) is directed toward the electron beam irradiator 24, and thus, this remaining portion of this vessel 4 and one-half of the vessel 4 carried by the lower vessel holder 26 which is located toward the electron beam irradiator 24 are subject to the irradiation of the electron beam which takes place across the upper and the lower end of these two vessels 4 to be sterilized. It will be seen that the vessel 4 which is carried by the upper vessel holder 26 is subject to the irradiation of the electron beam two times, namely, when it is located downward and when it is inverted and then located upward, and thus it follows that the entire outer peripheral surface has been sterilized.

After passing through the electron beam irradiation position E, the vessel holder means 14 undergoes the upright transfer interval which extends from the vessel feed position A to the inversion start position C, and then the inversion interval C-D again, whereby the inversion takes place in accordance with the locus of the guide rail 62. Specifically, the holder 26 which assumed the upper position moves to its lower position while the holder 26 which assumed a lower position moves to its upper position, the vessel having its entire surface sterilized is carried in its lower, erect position while the vessel 4 having one-half surface which is located radially outward of the revolving body 12 assumes an inverted position with the sterilized surface directed radially inward.

When the vessel holder means 14 passes through the inversion interval C-D and comes to the vessel discharge position B, the vessel 4 carried by the lower vessel holder 26 is now carried by the gripper 20 of the discharge gripper wheel 18 to be taken out of the vessel holder 26 and then rotatively conveyed to be discharged onto the air conveyor 22. The vessel holder means 14 travels while only the upper vessel holder 26 carries the vessel 4 in a path section from the vessel discharge position B to the vessel feed position A, where the vessel 4 is handed to the lower vessel holder 26 from the gripper 8 of the feed gripper wheel 6. In this manner, the single vessel 4 is conveyed so that it passes through the electron beam irradiation position E and the inversion interval twice as the revolving body 12 of the electron beam sterilizer 10 revolves, and is subject to the irradiation of the electron beam by passing the frontage of the irradiation unit 24 of the electron beam irradiator under two conditions that it is carried by the lower vessel holder 26 in an erect position and carried by the upper vessel holder 26 of the vessel holder means 14 in an inverted position. As a consequence, only the single electron beam irradiator 24 is provided, the entire outer peripheral surface of the vessel 4 can be completely sterilized while it is continuously conveyed. In addition, this allows a reduction in the size and the cost of the sterilizer while enabling a high speed operation. It is to be noted that while the electron beam irradiation position E is located between the vessel feed position A and the inversion start position C, it is not limited to such position, but may be chosen to be located within the upright transfer interval from the position D where the inversion interval ends to the vessel discharge position B.

Figure 6:
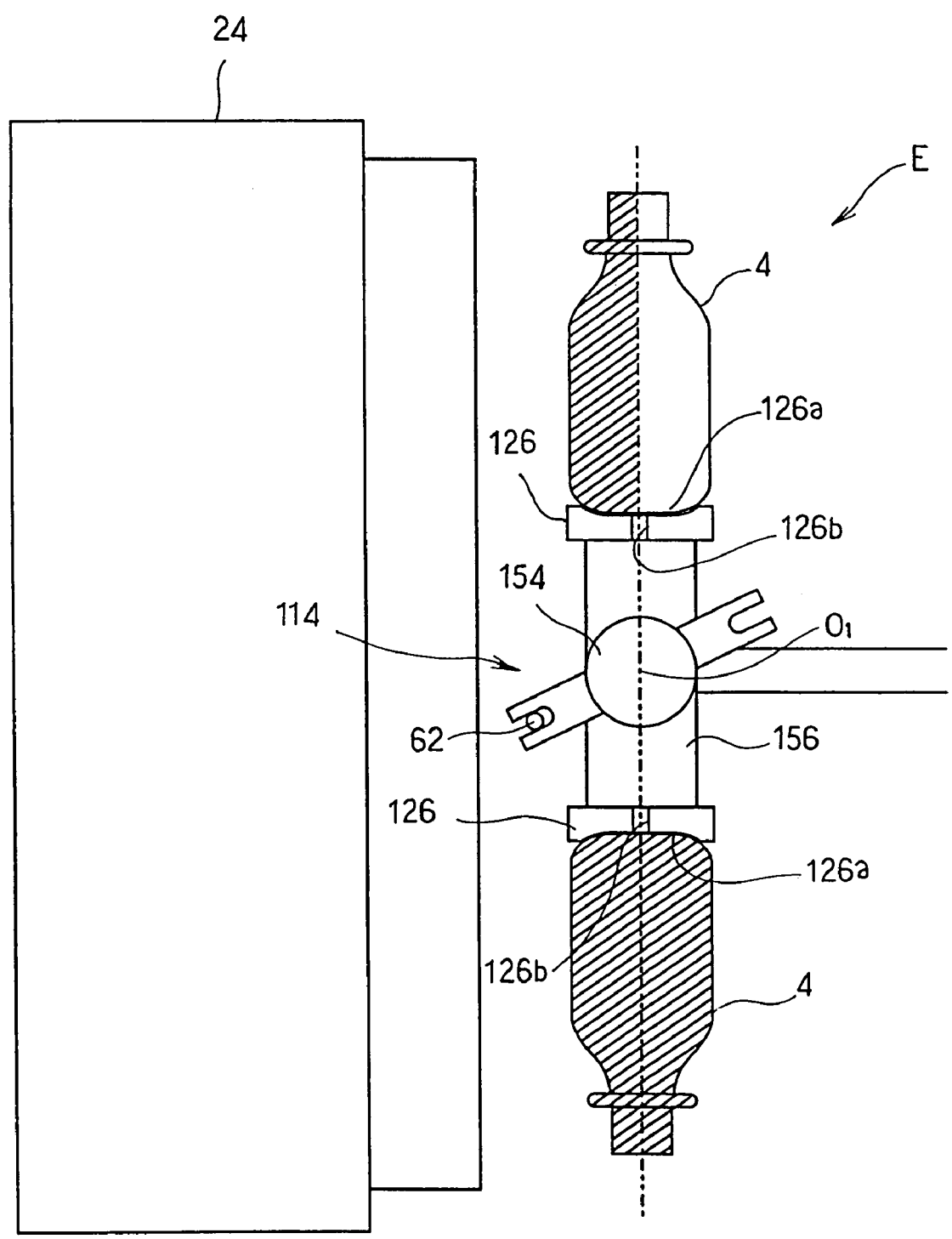
FIG. 6 is a longitudinal section of an essential part of an electron beam sterilizer according to a second embodiment of the present invention.

FIG. 6 is a longitudinal section of an electron beam sterilizer according to a second embodiment, taken at an electron beam irradiation position E where an electron beam irradiator is disposed, in a manner corresponding to FIG. 3 for the first embodiment. This embodiment differs from the first embodiment only in respect of the construction of the vessel holder means and is similar in other respects. Accordingly, only the difference will be described, and remaining parts will not be described while using similar characters for the remaining parts. Vessel holder means 114 of this embodiment comprises vessel holders 126, 126 formed by vacuum tables and connected to the opposite ends of a pair of parallel support plates 156 which are centrally secured to the opposite ends of a rod 154.

The external surfaces of the both vacuum tables 126, 126 are formed with depressions 126a, 126a which substantially conform to the configuration of the bottom surface of vessels 4, 4 to be carried. The depressions 126a, 126a are centrally formed with vacuum openings 126b, 126b which are connected to a vacuum source, not shown. In this embodiment, the vessel feed means (conveyor) which conveys the vessels 4 is a top chain conveyor on which the vessels 4 are upstanding while they are conveyed, and the vessels are fed to the electron beam sterilizer 10 through a star wheel. The vessel carrying surfaces of the conveyor and the star wheel are substantially aligned with the upper surface of the vacuum table 126 of the vessel holder means 114, which represents the upper vessel holder, and the vessels 4 are fed to and discharged from the upper vacuum table 126.

The vessels 4 which are conveyed by the conveyor are handed through the feed star wheel to the upper vacuum table 126 of the vessel holder means 114 contained in the electron beam sterilizer 10. The vessel 4 which is placed on the vacuum table 126a is carried by a suction applied through the vacuum opening 126b. When the vessel holder means 114 reaches the electron beam irradiation position E located in front of an irradiation unit 24 of the electron beam irradiator while carrying the vessel 4 on the upper vacuum table 126, the vessel 4 is subject to the irradiation of the electron beam which is directed from the radially outside of the revolving body 12, whereby substantially one-half of the external surface is sterilized. A hatched part of the vessel 4 carried by the upper vacuum table 126 as shown in FIG. 6 represents a portion which is sterilized by the irradiation with the electron beam.

When the vessel holder means 114 travels rotatively as the revolving body 12 revolves and enters an inversion interval C-D to be inverted in the similar manner as in the first embodiment. In this embodiment, the vessel 4 which is externally fed is carried by the upper vacuum table 126, and accordingly, when it is inverted, it is then conveyed in its inverted position by having its bottom surface sucked by the lower vacuum table 126.

When it passes through the inversion interval C-D, then the discharge position B to reach the feed position A, the next succeeding vessel 4 is fed to the vacuum table 126 which then assumes the upper position. Subsequently when the vessel holder means 114 reaches the electron beam irradiation position E located in front of the irradiation unit 24 of the electron beam irradiator, the surfaces of the vessels 4 which are carried by the upper and the lower vacuum table 126, 126 which are located toward the irradiation unit 24 are sterilized by irradiation with the electron beam. The vessel 4 carried by the lower vacuum table 126 is subject to the second irradiation while the vessel 4 carried by the upper vacuum table 126 is subject to the first irradiation of the electron beam (hatched portions of the two upper and lower vessels 4 shown in FIG. 6 represent portions which are irradiated with the electron beam). In the second embodiment also, the vessels 4 are subject to the inversion about the tangential axis of the revolving body 12 (or the center axis of the rod 154) and are subject to the irradiation with the electron beam from the electron beam irradiator 24 twice at their upper and lower positions in the similar manner as in the first embodiment, whereby the entire outer peripheral surfaces of the vessels 4 can be sterilized while they are continuously conveyed.

Figure 7:
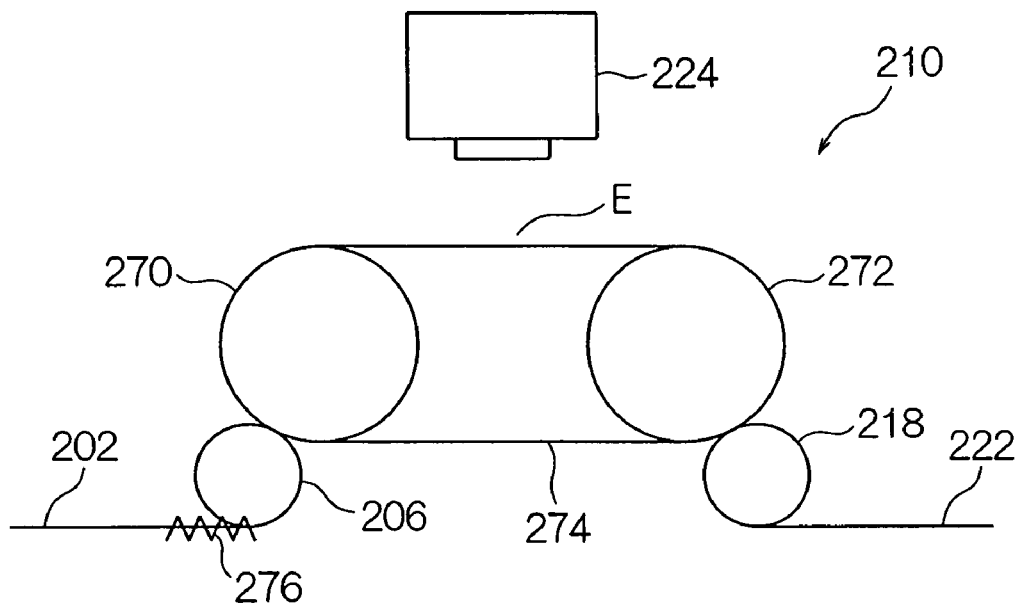
FIG. 7 is a plan view showing an overall arrangement of an electron beam sterilizer according to a third embodiment in a simplified form.

In the electron beam sterilizer 10 according to each of the embodiments described above, vessel holder means 14, 114 are provided around the revolving body 12 at an equal circumferential spacing to convey rotatively the vessels 4 which are carried by the vessel holder means 14, 114 as the revolving body 12 revolves to perform the inversion of the vessels 4 and the irradiation with the electron beam. However, the transfer means which cyclically performs the transfer of the vessel holder means 14, 114 which carry the vessels 4 is not limited to one which causes a rotating movement along a circular path around the revolving body 12, but may be chosen to achieve a cyclic transfer along any given path. FIG. 7 is a plan view showing an overall arrangement of an electron beam sterilizer 210 according to a third embodiment where a plurality of vessel holder means (not shown) are provided at an equal interval on a chain 274 which is disposed to extend around an upstream circular sprocket 270 and a downstream circular sprocket 272, each vessel holder means carrying two vessels in vertical alignment which are subject to an inversion between upper and lower positions during the time they are cyclically transferred around the both sprocket 270, 272.

An electron beam irradiator 224 is disposed on a linear path on which the vessels are conveyed, and an electron beam irradiation position E where the electron beam irradiator 224 is disposed is chosen to be within an upright transfer interval where vessel holder means carrying two vessels in vertical alignment are transferred. An inversion interval where the vessel holder means are inverted is chosen to be anywhere other than the electron beam irradiation position E. The location of the inversion interval may be on a linear conveying part between the both sprockets 270, 272, or may be in an interval where they are rotatively transferred around the sprockets 270, 272. When the inversion interval is chosen to be on the linear path between the sprockets 270, 272, the vessel holder means are rotated about an axis which is parallel to the direction in which the chain advances. When the inversion means is disposed in an interval where the vessels are rotatively transferred around the sprockets 270, 272, the vessel holder means are rotated about an axis which is tangential of the sprockets (revolving bodies) 270, 272, in the similar manner as in the first embodiment. The axis which is tangential to the revolving body is implied by the axis which is parallel to the travelling direction. The inversion means which causes an inversion of the two vessels between upper and lower positions may comprise the guide rail and the engaging member provided on the vessel holder means as in the first embodiment, but may also be constructed otherwise.

In this embodiment, vessels which are conveyed by a vessel conveying conveyor 202 are separated into a given interval by an in-feed screw 276, handed to a feed wheel 206 and then fed to an electron beam sterilizer 210. The electron beam sterilizer 210 includes vessel holder means which convey vessels carried by a pair of upper and lower vessel holders. When passing the electron beam irradiation position E, the vessel is subject to the irradiation of the electron beam in its upright position twice, namely, when it assumes a lower position and when it assumes an upper position. Vessels which are carried by the vessel holders and conveyed substantially twice along the circulating path to be subject to the irradiation with the electron beam twice are then handed to a discharge wheel 218 to be discharged from the electron beam sterilizer 210 and then conveyed by a conveyor 222 to a succeeding step. In this embodiment also, the electron beam irradiator 224 disposed at a single location allows the full periphery of the vessel to be sterilized in the similar manner as in the described embodiments, allowing a simplification of the construction of the sterilizer.

Figure 8:
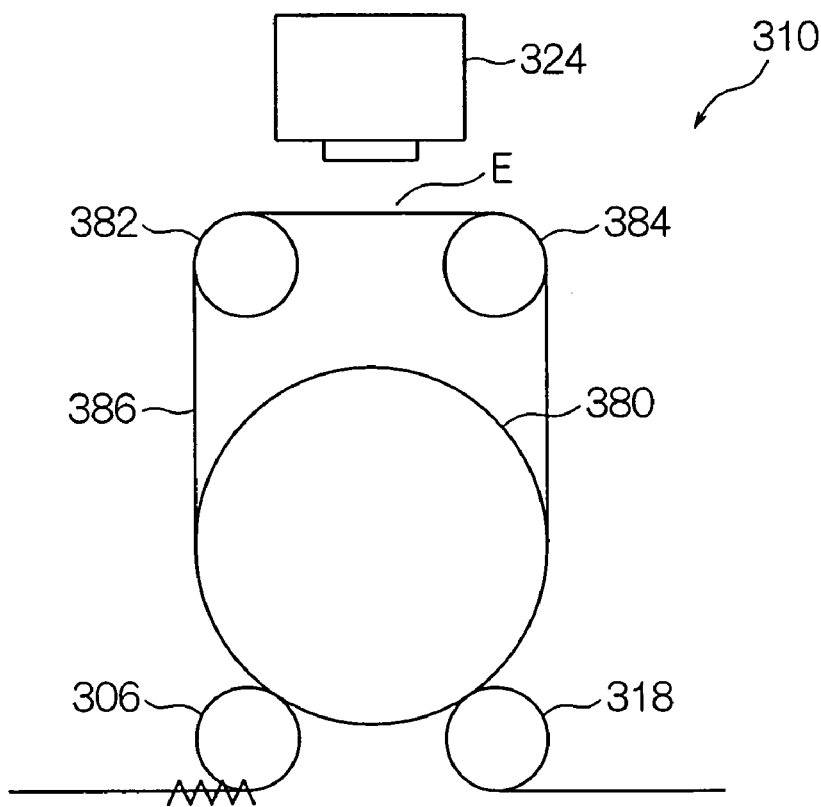
FIG. 8 is a plan view showing an overall arrangement of an electron beam sterilizer according to a fourth embodiment in a simplified form.

FIG. 8 is a schematic view showing an arrangement of an electron beam sterilizer 310 according to a fourth embodiment. In this embodiment, a transfer path for the vessel holder means which carry the vessels is different from each of the described embodiments, but in other respects, the arrangement is similar to the previous embodiments, and therefore will not be described. In this embodiment, a sprocket 380 of a large diameter is disposed in opposing relationship with a feed wheel 306 and a discharge wheel 318, and a chain 386 is disposed around the sprocket 380 and two sprockets 382 and 384 of a reduced diameter, and the vessels carried by the two vessel holders of the vessel holder means are cyclically conveyed around the three sprockets 380, 382 and 384.

An electron beam irradiator 324 is disposed in an interval between the two sprockets 382, 384 of a reduced diameter where the vessels are linearly conveyed. The electron beam irradiation position E where the irradiation of the vessels with the electron beam takes place by the electron beam irradiator 324 is located in an upright transfer interval where the two vessels carried by the vessel holder means are disposed in an upright position and in vertical alignment, and an inversion interval where an inversion of the vessel holder means between upper and lower positions is chosen at a location other than the electron beam irradiation position E. The inversion interval may be chosen in a linear conveying part where the vessels are linearly conveyed between the sprockets 380, 382, 384, or may be chosen in an interval where the vessels are rotatively conveyed around the sprockets 380, 382, 384. Alternatively, the inversion interval may be chosen to include both the linear conveying path and the rotatively conveying path. In this embodiment also, similar effects and functions are achieved as in the previous embodiments.

What is claimed is:

1. An electron beam sterilizer which sterilizes vessels being conveyed by irradiation with an electron beam, comprising vessel holder means including a pair of holders which carries two vessels in vertical alignment, transfer means on which a plurality of vessel holder means are mounted at an equal spacing and cyclically transferred, inversion means for inverting the vessel holder means by rotating it about an axis parallel to a direction in which the transfer means advances, and an electron beam irradiator capable of irradiating the electron beam across the upper and the lower end of the two vessels which are carried in vertical alignment by the vessel holder means, the arrangement being such that a transfer path of the transfer means extends from a vessel feed position to a vessel discharge position and includes an inversion interval where the inversion means inverts the vessel holder means and an upright transfer interval where the vessels in vertical alignment are transferred in an upright position, the electron beam irradiator having an electron beam irradiation position which is chosen to be within the upright transfer interval, the vessels which are fed through the vessel feed position being discharged at the vessel discharge position after passing through the electron beam irradiation position and the inversion interval twice.

2. An electron beam sterilizer according to claim 1 in which the inversion means comprises a guide rail disposed along a transfer path for the vessel holder means, and an engaging member mounted on the vessel holder means and engaging the guide rail.

3. An electron beam sterilizer according to claim 1 in which the holder of the vessel holder means comprises a pair of holding plates which are attracted toward each other by springs, the holding plates being effective to hold a neck of a vessel sandwiched therebetween.

4. An electron beam sterilizer according to claim 1 in which the holder of the vessel holder means comprises a vacuum table which applies a vacuum suction for holding the vessel by sucking the bottom surface thereof.

5. An electron beam sterilizer according to claim 1 in which the electron beam irradiation position is chosen to be between a feed position where vessels are fed to the transfer means and a start position of the inversion interval.

6. An electron beam sterilizer according to claim 1 in which the electron beam irradiation position is chosen to be between an end position of the inversion interval and the discharge position where vessels are discharged from the transfer means.

* * * * *